(12) United States Patent
Hall et al.

(10) Patent No.: US 9,766,257 B1
(45) Date of Patent: Sep. 19, 2017

(54) TOILET THAT DETECTS FLUORESCENT DRUG MARKERS AND METHODS OF USE THEREOF

(71) Applicants: David R. Hall, Provo, UT (US); Conrad Rosenbrock, Provo, UT (US); Ben Swenson, Lehi, UT (US); Daniel Hendricks, Provo, UT (US); Joe Fox, Spanish Fork, UT (US); Terrece Pearman, Draper, UT (US)

(72) Inventors: David R. Hall, Provo, UT (US); Conrad Rosenbrock, Provo, UT (US); Ben Swenson, Lehi, UT (US); Daniel Hendricks, Provo, UT (US); Joe Fox, Spanish Fork, UT (US); Terrece Pearman, Draper, UT (US)

(*) Notice: Subject to any disclaimer, the term of this patent is extended or adjusted under 35 U.S.C. 154(b) by 0 days.

(21) Appl. No.: 15/497,638

(22) Filed: Apr. 26, 2017

Related U.S. Application Data

(63) Continuation-in-part of application No. 15/361,872, filed on Nov. 28, 2016, now Pat. No. 9,671,343.

(51) Int. Cl.
| | |
|---|---|
| *G01N 21/64* | (2006.01) |
| *E03D 11/11* | (2006.01) |
| *E03D 11/13* | (2006.01) |
| *G01N 33/493* | (2006.01) |
| *G01N 33/94* | (2006.01) |
| *A61B 10/00* | (2006.01) |

(52) U.S. Cl.
CPC ............ *G01N 33/94* (2013.01); *A61B 10/007* (2013.01); *E03D 11/11* (2013.01); *E03D 11/13* (2013.01); *G01N 21/6428* (2013.01); *G01N 33/493* (2013.01); *G01N 2021/6417* (2013.01); *G01N 2201/061* (2013.01)

(58) Field of Classification Search
CPC ....... A61B 10/007; E03D 11/11; E03D 11/13; G01N 2021/6439; G01N 21/6428; G01N 21/645; G01N 33/493
See application file for complete search history.

(56) References Cited

U.S. PATENT DOCUMENTS

| | | | | |
|---|---|---|---|---|
| 6,068,981 | A * | 5/2000 | Rittenburg | G01N 33/5308 424/457 |
| 2015/0359522 | A1* | 12/2015 | Recht | G01N 33/62 600/573 |
| 2016/0299061 | A1* | 10/2016 | Goldring | G01J 3/0291 |

* cited by examiner

*Primary Examiner* — Mark R Gaworecki

(57) ABSTRACT

The present disclosure describes a method of detecting a drug marker in urine a urine sample using a toilet. The drug markers are fluorophores each of which emits a unique fluorescence spectra. Accordingly, the method does not detect the drug but rather, the drug marker. The drug marker may include quantum dots which may be functionalized by connecting the quantum dot to a biomolecule. The biomolecule may be cleavable by a peptidase, a protease, or a nuclease to release the drug. Alternatively, the composition may include a liposome carrier. A user who has consumed the drug composition urinates into the toilet and a urine sample is captured. The toilet includes a mechanism for fluid handling which diverts urine into a fluorescence spectrometer. The fluorescence spectrometer screens the urine for drug markers based on their unique fluorescent spectra.

20 Claims, 11 Drawing Sheets

TOILET THAT DETECTS FLUORESCENT DRUG MARKERS AND METHODS OF USE THEREOF

CROSS REFERENCE TO RELATED APPLICATIONS

This application is a continuation-in-part of co-pending U.S. patent application Ser. No. 15/361,872 filed on Nov. 28, 2016 which is hereby incorporated by reference in its entirety.

FIELD OF THE INVENTION

This invention relates to devices for detecting and quantifying drugs in a user's bodily fluids or bodily waste and methods of use thereof.

BACKGROUND OF THE INVENTION

Detection of drugs after consumption is useful for many purposes including detection of illicit drug use, verification of prescription drug consumption, detection of drug consumption to avoid potential interference from contraindicated drugs, monitoring pharmacokinetic rates, dosage adjustment and many others. Drug testing typically involves urine or blood sampling, and in some cases saliva testing. In some situations a quantitative measurement is needed while in others, a qualitative presence detection is sufficient.

Drugs may be detected in an individual's bodily fluids or bodily waste by several methods. These include colorimetric assays, immunoassays, chromatography, and other chemical detection methods. Each of these methods is associated with its own limitations.

Convenient methods of drug detection and quantification include detection of the drug or drug metabolite in urine or saliva. However, detection and measurement of a drug by colorimetric or immunoassay methods typically requires development of a custom assay for each chemical or biochemical target. This means that a detection assay must be developed specifically for each drug or class of drugs. Developing a custom assay limits drug detection to high risk drugs of abuse or very common drugs for which a large enough market exists. More specifically, the need for the assay must be worth the cost of developing the assay. Alternatively, separation and detection techniques, including chromatography may be used. However, these techniques require complex lab equipment and calibration.

An alternative method to detect and/or quantify the presence of a drug in an individual's body is to put a marker in the drug, the marker having a detectable signature or characteristic. This technique alleviates the need to directly measure the drug or the drug metabolites. With this technique, the problem simplifies to developing methods to detect the marker instead of the drug or drug metabolite. Because there are many available drugs, many different markers are needed for to distinguish between different drugs. The markers may have one or more distinguishing characteristic so that the identity of each drug may be determined and the simultaneous presence of multiple drugs may be detected. Ideally, the markers may be biocompatible and not significantly biodegradable. They may have an easily detected signature and not interfere with the efficacy of medically useful drugs. For convenience, the markers may be cleared from the body through urine. Markers that meet these specifications and a device to conveniently identify and quantify the markers in urine is needed.

SUMMARY

We disclose a novel method for inferring the identity and quantity of drugs consumed by a user by detecting a fluorescent drug marker in the urine of a user. The analytical instrument used in the method is a toilet into which the user urinates as the user would normally do when using a traditional toilet. This method provides a level of convenience that does not exist with traditional drug testing methods.

The method includes providing a user who consumes a composition which includes a drug and a fluorescent drug marker. Each fluorescent drug marker possesses a unique fluorescence emission spectra and each drug is compounded with a different drug marker. By detecting the fluorescence emission spectra and matching it to the fluorescent signatures of known drug markers, the presence of the drug associated with that drug marker may be inferred.

The method further includes the use of a toilet which a user may easily and conveniently urinate into, as when using a traditional toilet. However, the toilet disclosed herein is unique at least because it includes a fluid handling system which collects a urine sample and diverts it into a fluorescence spectrometer for analysis. More specifically, the fluid handling system transfers the urine sample from a urine capture reservoir to a fluorescence measurement cell. The fluorescence measurement cell is a component of a fluorescence spectrometer that is within the toilet. The fluorescence spectrometer performs the steps of directing a filtered light source of a defined wavelength or range of wavelengths into the fluorescence measurement cell. The drug marker in the urine sample absorbs the light and emits light of a different wavelength. The fluorescence emission spectrum is measured and compared to known fluorescent signatures of the different drug markers in use.

The disclosed method identifies the drug the user consumed without directly measuring the drug itself or its metabolites. Measuring the fluorescence emission spectra of drugs in the urine replaces the need to measure the drug itself because each drug is compounded with a unique fluorescent drug marker and because each unique drug marker emits a distinguishable fluorescent signature. This solution removes the need to develop a new analytic tool for each drug. Applying the intensity of the fluorescent signals to standard curves further provides estimates of the amount of drug marker in the urine.

The toilet may further include one or more mechanisms for identifying the user. In some embodiments, the toilet may include a controller connected to the toilet which may link the measurements performed on each user's urine to the user's identity. In this embodiment, the method includes the steps of actuating the user identification mechanism so that the results of the urine analyses are stored in a file that collects that user's results. Repeated measurements may be collected and stored for multiple users with the results for each user readily identifiable. The controller may transfer stored data to a network database which may then be downloaded to a remote processor for analysis. The data may be analyzed by healthcare provider, law enforcement, and others for purposes that include determining whether a user is compliant in taking his or her medication, determining whether the user has accidentally consumed a drug in the wrong amount, determining whether a user has consumed drugs that are inappropriate or not prescribed to that user, estimating the severity of a drug overdose, estimating pharmacokinetic properties of a drug, and detecting illicit drugs in a user's body.

DETAILED DESCRIPTION

Definitions

Figure 1A:
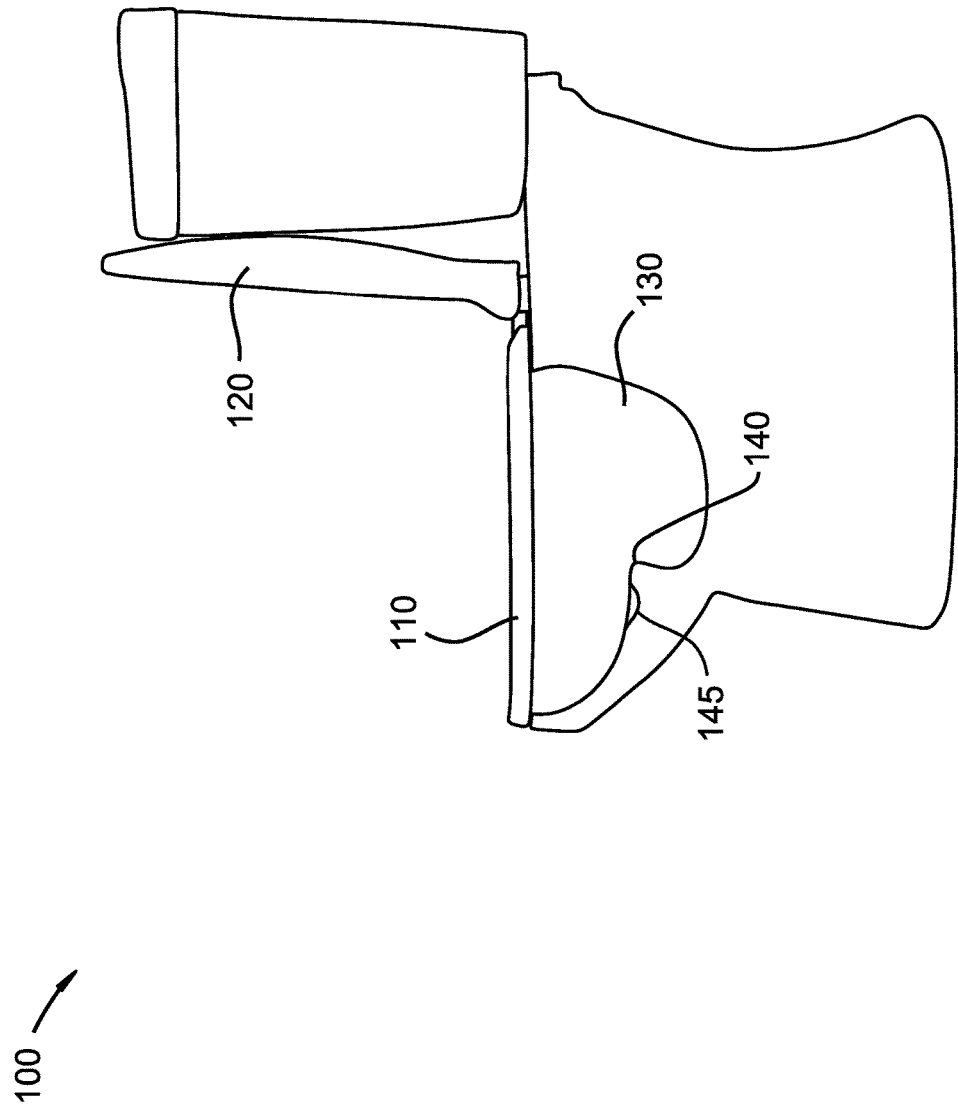
FIG. 1A is a cross sectional view of a toilet according to an embodiment of the invention.

Drug, as used herein, means a medication which may be used for legitimate medical treatment, illicit bioactive substances which may or may not have a legal and legitimate medical use, both prescription and nonprescription substances, and both natural and synthetic substances. The terms "medicine" and "medication" are included in the definition of "drug" as used herein. In some embodiments, the drug may be a small molecule. In other embodiments, the drug may be a peptide or antibody.

Toilet, as used herein, means a device that may be used to collect one or more biological waste products of a user. This may include a traditional water toilet. However, toilet, as used herein, may mean any device which may be used to collect bodily waste according to the present disclosure and which may be equipped to analyze bodily waste according to the present disclosure.

User, as used herein, means a human or animal that deposits bodily waste into an embodiment of the toilet disclosed herein.

Consumed, as used herein with regard to drugs, means oral, intravenous, intramuscular, intraperitoneal, sublingual, subcutaneous, transdermal, or nasal administration of the drug or any other route of administration which would cause a drug to be metabolized in the body.

Disclosed herein is a method of identifying what drug or drugs a user has consumed by measuring a fluorescent drug marker in the user's urine. The measurement is performed using a toilet equipped with a fluorescence spectrometer. The toilet used in the disclosed method comprises a fluid handling system for collecting a urine sample as the user urinates normally into the toilet. The fluid handling system samples the user's urine and diverts it into a fluorescence spectrometer which may be located on or within the toilet. The fluorescence spectrometer measures the fluorescence spectra emitted by one or more drug markers in the urine sample. The fluorescence signal may be proportional to the amount of drug that entered the user's body and which was cleared by the renal system. Therefore, not only may the presence of the fluorescent signal indicate that the user consumed the drug but the intensity of the fluorescent signal may be used to estimate the quantity of drug consumed.

This system has a variety of uses including, but not limited to, determining whether a user is compliant in taking his or her medication, determining whether the user has accidentally consumed a drug in the wrong amount, determining whether a user has consumed drugs that are inappropriate or not prescribed to that user, estimating the severity of a drug overdose, estimating pharmacokinetic properties of a drug, and detecting illicit drugs in a user's body.

The fluorescent signal may be generated by a fluorescent marker mixed with or connected to the drug to form a composition. The drug may be connected to the fluorescent marker through a variety of mechanisms. These include covalent or noncovalent bonding and encapsulating the drug in a carrier that emits a fluorescent signal before or after releasing the drug from the carrier.

An example of a carrier is a clathrate containing a fluorescent marker. According to the disclosure, the clathrate may be a lattice "cage" that traps the drug inside. The clathrate lattice may comprise the fluorescent molecule or the fluorescent molecule may be inside the clathrate lattice. In some embodiments, the clathrate is a nanodisc clathrate.

In other embodiments, the carrier may comprise a liposome. The drug may be inside the liposome. In some embodiments, more than one drug is inside the liposome. In some embodiments, the fluorescent drug marker is in the center of the liposome along with the drug. In other embodiments, the fluorescent drug marker is part of the liposome's lipid layer. Fluorescent molecules that have hydrophobic properties may be optimally incorporated in the liposome's lipid layer whereas more hydrophilic fluorescent markers may be optimally placed in the center of the liposome.

In some embodiments, the liposome may include ligands which target the liposome to a specific tissue. The specific tissue may be a tissue which is the target of the drug. Consequently, the liposome delivers the drug to the tissue with which the drug is intended to interact.

Another drug marker candidate is a quantum dot, a nanoscale semiconductor with size-dependent fluorescence emission. The quantum dot marker may be suitable for consumption and may be synthesized and solubilized with sufficient homogeneity to create quantum dot solutions with many different fluorescence emission bands for use as drug markers.

Quantum dots may be passivated, functionalized, or encapsulated to achieve a relatively chemically inert fluorescence marker. The quantum dot solutions may include the drug, or in some embodiments, the quantum dot may be encapsulated or functionalized with biomolecules by coating the quantum dot to a biomolecule. The biomolecule may include a hydrogel, a protein, a peptide, a DNA molecule, an RNA molecule, or an antibody. In some embodiments, the DNA molecule comprises a non-genomic DNA sequence and/or a non-naturally occurring peptide sequence. In embodiments where the quantum dot is functionalized and/ or encapsulated using a DNA molecule, the DNA molecule may include one or more nucleotide cleavage sites. The nucleotide cleavage sites may be cleaved by a nuclease and the drug released. In some embodiments, the nucleotide cleavage site may be a restriction endonuclease cleavage site. Because restriction endonucleases are produced by bacteria, in some embodiments the bacteria in the user's gastrointestinal tract may cleave the DNA molecule at the restriction endonuclease cleavage site causing the drug to be released. The drug may then be absorbed by the intestine and perform its intended biological function on the user leaving the drug marker to be cleared by the renal system and measured in urine.

In some embodiments in which the quantum dot may be functionalized or encapsulated by a DNA molecule or RNA molecule, the DNA or RNA molecule may be cleaved by a eukaryotic nuclease. In some embodiments, the DNA or RNA may be single stranded and cleaved by a eukaryotic single strand nuclease. Examples of eukaryotic single strand nuclease which may be cleave the single stranded DNA or RNA according to the disclosure include zinc finger nuclease, RNAse H2, pancreatic nuclease, and p53.

In some embodiments, the DNA molecule may be double stranded and cleaved by a eukaryotic double strand nuclease including DNAse I.

In embodiments in which the quantum dot is functionalized or encapsulated by a protein or peptide, the protein or peptide may include a protease cleavage site. Endogenous proteases that are present in the user's body may cleave the protein or peptide at the protease cleavage site. The drug may then be released and perform its intended biological function. In embodiments in which the quantum dot includes an antibody, the antibody may also include a peptidase cleavage site which may be cleaved as described above.

In some embodiments, the protease cleavage site is cleaved by a eukaryotic protease produced by the user's body. In some embodiments, the eukaryotic protease may be a metalloprotease, a serine protease, or a digestive protease. Metalloproteases and serine proteases are found in mammalian blood and function in the management of thrombosis. Examples of serine proteases in blood include thrombin, plasmin, and urokinase. In embodiments in which the protease cleavage site is cleaved by a metalloprotease or serine protease, the drug and fluorescent drug marker may be released into the user's blood.

Digestive proteases may be found in the stomach. They may function to directly digest food or to activate proteins that assist in gastrointestinal function. Examples of digestive proteases include gastrin, pepsin, trypsin, and chymotrypsin.

In some embodiments, the quantum dot is functionalized and/or encapsulated with a peptide or protein and the peptide or protein is bound to a nucleotide sequence. The peptide, protein, DNA, or both may be cleaved by appropriate enzymes to release the drug.

In some embodiments, the biomolecule is cleaved by a glycoside hydrolase. Lysozyme is an example of a glycoside hydrolase. Lysozyme functions in mammals as an antimicrobial enzyme and is found in secreted fluids as well as in macrophages and polymorphonuclear neutrophils.

Mammalian bodies include prokaryotic cells which produce enzymes which may cleave the biomolecules according to the disclosure. For example, the colon includes the bacteria *Escherichia coli* (*E. coli*). Enzymes produced by *E. coli* include nucleases, including exonuclease I, exonuclease IV, RNAse A, and RNAse I.

In some embodiments, the biomolecule includes a hydrogel. In some embodiments, the hydrogel comprises more than one drug. The hydrogel may be cleaved in a low pH solution to release the drug and the fluorescent drug markers. In some embodiments, the hydrogel may be cleaved in a solution that has a pH of between about 1.0 and about 3.0. An example of a bodily solution which may be within this pH range includes gastric secretions. Consequently, the drug and fluorescent drug marker may be released in the stomach.

The fluorescent drug molecule may be separated from the drug after the biomolecule is cleaved as described above. The DNA, RNA, peptide, antibody, or other biomolecule may be engineered to include the desired cleavage site. For example, the DNA molecule used to functionalize the quantum dots may be a non-genomic sequence that includes a restriction enzyme cleavage site. Alternatively, in embodiments in which a peptide is used to functionalize the quantum dots, the peptide sequence may be a non-naturally occurring peptide sequence into which a peptidase cleavage site has been engineered. While the newly released drug may be metabolized to one or more byproducts that are difficult to measure, the fluorescent marker may be cleared by the urine independent from the drug and its metabolites. Consequently, the drug marker may be detected by the fluorescent spectrometer in or on the toilet regardless of the fate of the drug molecule.

The markers in different drugs may have one or more distinguishing characteristic, including different fluorescence emission spectra, so that the drug marker may be identified and distinguished from markers associated with drugs. Consequently, in situations when a user has consumed more than one drug, the unique fluorescent signal of each drug may enable quantification of each individual drug in the presence of the other drugs. Furthermore, the markers may be used in combination to build a unique code which identifies the combination of drugs consumed by a user and their respective quantities. Multivariate analysis may be used to disambiguate the signatures of multiple drugs.

The disclosure describes a mechanism for rinsing the fluid handling system and fluorescence measuring cell after each use to prevent cross contamination of samples. As described in more detail below, the rinsing device flushes water from a water source through the fluorescence measuring cell and through the fluid handling system up to the orifice in the urine capture reservoir. The rinsing device may include a valve, a pump, or both to regulate water from the water source.

The disclosure includes mechanisms for user identification. The toilet may identify the user as the user approaches through a wireless system which may be the user's mobile device. Alternatively, the user may sit on, or otherwise interact with the toilet which may take biological measurements, including body weight, blood pressure, or bioimpedance measurement, which may be unique to the user and thereby identify the user. A user may also manually enter identification information which may comprise entering a code into a key pad to identify the user. By identifying each user, a controller that may be included in the toilet may associate the results of the urine analysis with the user who provided the urine sample.

A controller in or connected to the toilet may record fluorescent measurements. In embodiments which include a mechanism to identify the user, the controller may associate each user with the data collected from that user's urine. The data may be uploaded to a network either wirelessly, through an Ethernet, or through other mechanisms known in the art. The data may then be downloaded to a computer at a remote location for further analysis and use.

The disclosure includes a method for detecting at least one drug marker in a user's urine after the user has consumed a composition. The method includes the steps of administering a composition to the user which includes a drug and a fluorescent drug marker as described herein. The fluorescent drug marker may emit a unique fluorescence emission spectra relative to other fluorescent drug markers that may be present in compositions that include other drugs when exposed to light of a defined wavelength. The method includes the step of providing a toilet that includes a urine capture reservoir and a fluorescence spectrometer. The fluorescence spectrometer may include one or more light sources, one or more fluorescence measurement cells, and a spectral analyzer. The urine capture reservoir may be connected to the fluorescence measurement cells in the fluorescence spectrometer by a channel. Urine may travel through the channel from the urine capture reservoir to the fluorescence measurement cell where it is spectral properties are analyzed.

In some embodiments, the method uses a toilet that includes a controller. The controller may include a connected to the fluorescence spectrometer and include a non-transitory computer readable medium for processing the data collected by the fluorescence spectrometer.

The method further includes the step of depositing the urine sample in the toilet. The toilet may comprise of embodiments disclosed herein. The user may urinate into the toilet normally as with a traditional toilet. This step provides a level of convenience that is not available with other methods of assessing drug use. The fluorescence spectrometer may then be actuated. In some embodiments, the controller actuates the fluorescent spectrometer. The fluorescence spectrometer then exposes the urine sample within the fluorescence measuring cell to light of the defined wavelength and collects a fluorescence emission spectra reading from the urine specimen. The spectral analyzer then analyzes the fluorescence emission spectra reading.

The fluorescence emission reading may then be transferred to the controller. Non-transitory computer readable medium within the controller may identify the drug by comparing the fluorescence emission spectra reading with the unique fluorescence emission spectra of known drug markers. Upon matching the fluorescence emission spectra reading with that of a known drug marker, the controller may determine the identity of the drug marker. The identity of the drug marker may be extrapolated to determine the identity of the drug.

The non-transitory computer readable medium within the controller may also perform the step of quantifying the fluorescent drug marker. This may be accomplished by applying the intensity of the fluorescence emission spectra reading to a standard curve for the fluorescent drug marker that is stored in the controller. By quantifying the fluorescent drug marker in the urine sample, the amount of drug the user has consumed may be estimated.

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Referring to FIG. 1A, toilet 100 is an embodiment of the disclosed toilet. Similar to traditional toilets, toilet 100 includes seat 110, lid 120, and toilet bowl 130. Toilet 100 further includes urine capture reservoir 140 which is shown in FIG. 1A as a raised mound. The mound of urine capture reservoir 140 is a protrusion of the inner surface of toilet bowl 130. The mound creates a ledge for capturing urine which, in the absence of the mound, would fall directly into the toilet water or run down the relatively vertical sides of the toilet bowl. In some embodiments, urine capture reservoir 140 is positioned near the front of the toilet relative to the user which is on the side of the toilet bowl that is furthest from the trap.

FIG. 1A further illustrates depression 145 on the upper side of the mound of urine capture device 140. Depression 140 allows urine flowing over the mound to pool for a short time and enter the urine analysis system through orifice 150 (first presented in FIG. 1B).

In some embodiments, the urine capture reservoir includes a urine detection sensor which detects urine in the urine capture reservoir. The urine detection sensor may be connected to a controller which actuates the fluorescence spectrometer when urine is present in the urine capture reservoir. Examples urine detection sensors include, but are not limited to, optical sensors and thermal sensors.

Figure 1B:
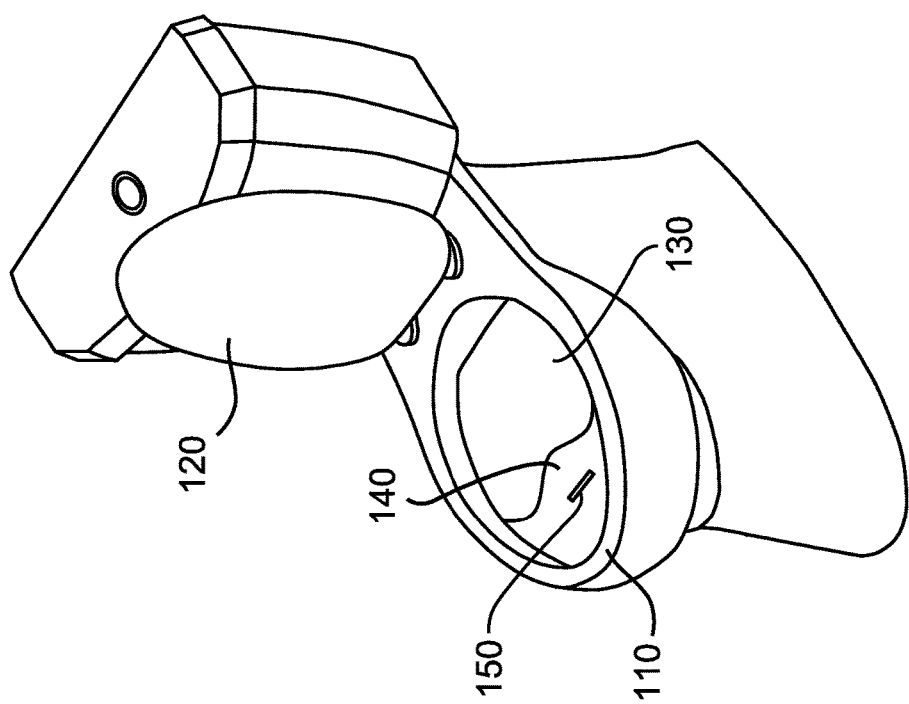
FIG. 1B is a perspective view of a toilet according to an embodiment of the invention.

FIG. 1B illustrates toilet 100 with an illustration of orifice 150 on the upper surface of urine capture device 140. In the embodiment of FIG. 1B, orifice 150 is shown as a slit. The slit may be constructed of two plates of glass positioned close together such that urine may be drawn through orifice 150 and into the urine analysis system by capillary action. In some embodiments, the length of the slit may range from approximately 2.5 mm to approximately 25 mm, or from approximately 2.5 mm to approximately 9.5 mm. In one embodiment, the length of the slit is about 6.35 mm. The height of the slit may, in some embodiments, range from approximately 2.5 mm to approximately 31.75 mm. In one embodiment, the height of the slit is approximately 6.35 mm. In some embodiments, the width of the slit may range from approximately 0.5 mm to approximately 2 mm. In some embodiments, the width of the slit may range from approximately 0.75 mm to approximately 1.5 mm. In some embodiments, the width of the slit is approximately 1 mm. In other embodiments, the orifice is not a slit or is a slit but is not narrow enough to draw urine in through capillary action. In these embodiments, urine may enter the orifice by gravitational action or by the action of a pump. The pump may be a syringe pump, a peristaltic pump, or other pump for moving liquid that is known in the art.

Figure 1C:
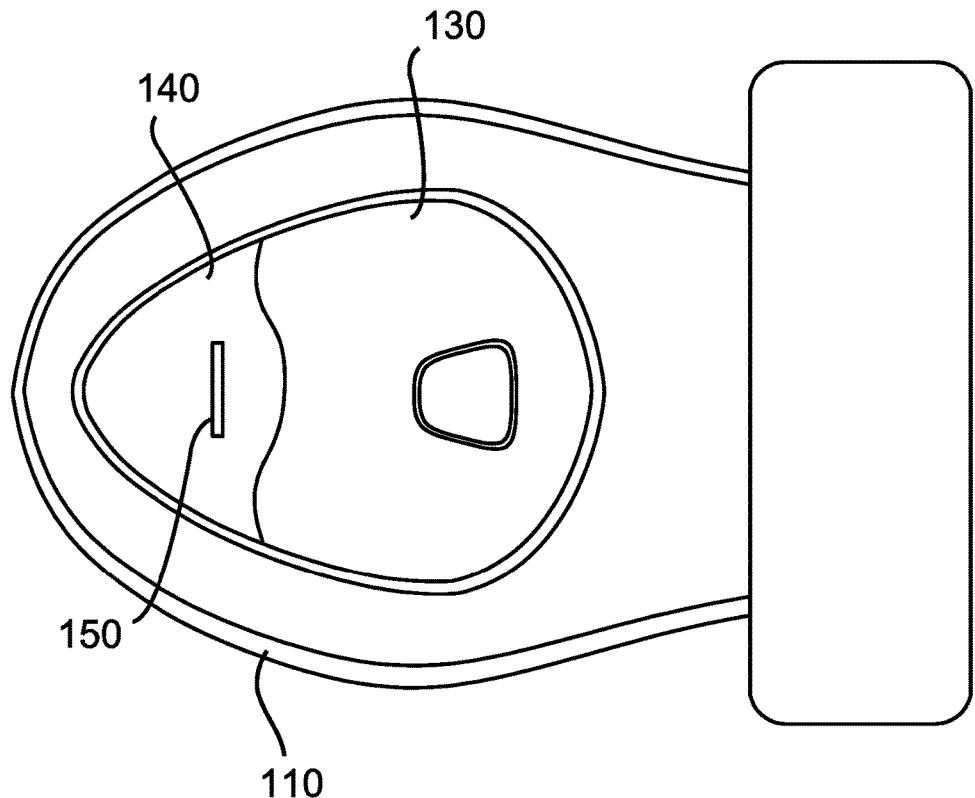
FIG. 1C is an aerial view of a toilet according to an embodiment of the invention.

FIG. 1C is a view of toilet 100 from the viewpoint of a user looking down towards toilet bowl 130. Orifice 150 is shown as a slit on the upper surface of the mound of urine capture device 140. In this embodiment, urine capture device 140 is positioned near the front of the toilet bowl furthest from the trap. A user urinates into toilet bowl 130 and onto urine capture device 140. Urine that flows over urine capture device 140 is delayed long enough for a sample to enter orifice 150 through one of the mechanisms described above.

Figure 2:
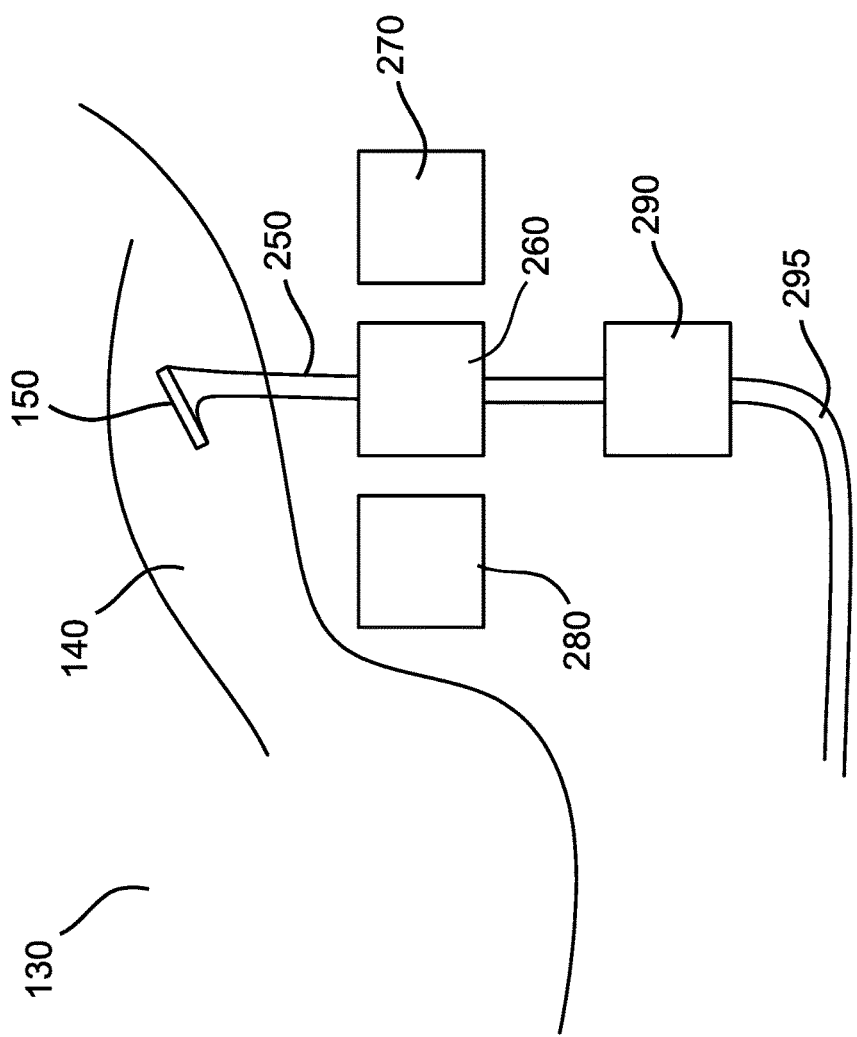
FIG. 2 is a schematic drawing of the components of the urine sampling and the fluorescence spectroscopy analysis systems according to an embodiment of the invention.

FIG. 2 illustrates a cross section of an embodiment of toilet 100. Orifice 150 leads into channel 250 which continues into fluorescence measurement cell 260 of a fluorescence spectrometer. Urine travels into orifice 150, through channel 250, and into fluorescence measurement cell 260 for analysis. In contrast, some embodiments include a section of the fluid handling system which functions as a fluorescence measurement cell. These embodiments include optical windows within the fluid handling system and below the orifice (shielded from ambient light) through which fluorescent signal may be measured in the same or similar manner as may be performed using the fluorescence measurement cell.

In some embodiments, the fluorescence measurement cell includes a thermal regulator. The thermal regulator makes it possible to detect certain temperature sensitive markers, a feature which adds an additional method through which to identify the presence different drugs. In addition, the thermal regulator may reduce the temperature to improve fluorescence emission quantum efficiency or achieve line-width narrowing. The thermal regulator may be connected to a controller which regulates the temperature within the fluorescence measurement cell.

FIG. 2 further illustrates fluorescence excitation light source 280 which emits light at multiple wavelengths. In some embodiments, fluorescence excitation light source 280 is a fluorescence pump light source. The fluorescence pump light source may be an ultraviolet laser, an ultraviolet light emitting diode (LED), or other fluorescence pump light sources known in the art. As will be described in more detail below, the multiple wavelengths are filtered before entering fluorescence measurement cell 260.

FIG. 2 also illustrates fluorescence spectral analyzer 270 which may detect dispersed (special or time domain) or filtered light. Fluorescence spectral analyzer 270 may conduct a multichannel or multi-element time or frequency domain analysis of the spectrum with sufficient resolution to detect multiple fluorophores. Examples include a compact optical grating spectrometer, a compact optical detected Fourier transform spectrometer, and a Michelson interferometer style Fourier transform spectrometer. Spectral analyzers may include a bandpass filter array, a tunable filter, and variations thereof known in the art. The spectral sensing band may be in the region 400-800 nm wavelengths, though it may extend to longer and shorter wavelengths. The resolution may be desirably approximately than 30 nm wavelengths, or less than 15 nm wavelengths, or less than 10 nm wavelengths. Better resolution allows for more independent fluorescence emission channels, down to the limit of the marker emission wavelength variation, which may intrinsic, environmental, or due to polydispersity. In some embodiments, the fluorescence spectrometer performs an ensemble measurement of many dispersed markers in the optical region. In some embodiments, the toilet has a detector for detecting the dispersed (spatial or time domain) or filtered light.

In some embodiments, the fluorescence measurement cell resembles that of a flow cytometer. Specifically, urine passes through a microfluidic channel of dimensions that may be approximately 100 microns in width. In some embodiments, the width is with a range of between approximately 10 microns and approximately 1000 microns. In some embodiments that comprise a microfluidic chamber, the fluorescence spectrometer may detect one fluorescent marker at a time. An ensemble distribution is created as a plurality of markers are analyzed serially. This technique has the advantage of measuring markers with more than one emission peak, including overlapping peaks, since measuring multiple markers in an ensemble measurement that is not performed by serial measurements would otherwise be ambiguous.

FIG. 2 also illustrates rinsing device 290 which is connected to tubing 295. Rinsing device 290 is connected to a water source through tubing 295. In some embodiments, the water source is refill water from the toilet tank. Rinsing device 290 diverts water from the water source though fluorescence measurement cell 260, channel 250, and orifice 150. This process removes residual urine from the system so that the next user's urine sample is not contaminated by that from the previous user. Rinse water from under the toilet rim as may be found in traditional toilets may also rinse the mound of urine capture device 140 so that a user's own urine stream does not wash urine from the previous user into orifice 150 causing contamination.

Figure 3A:
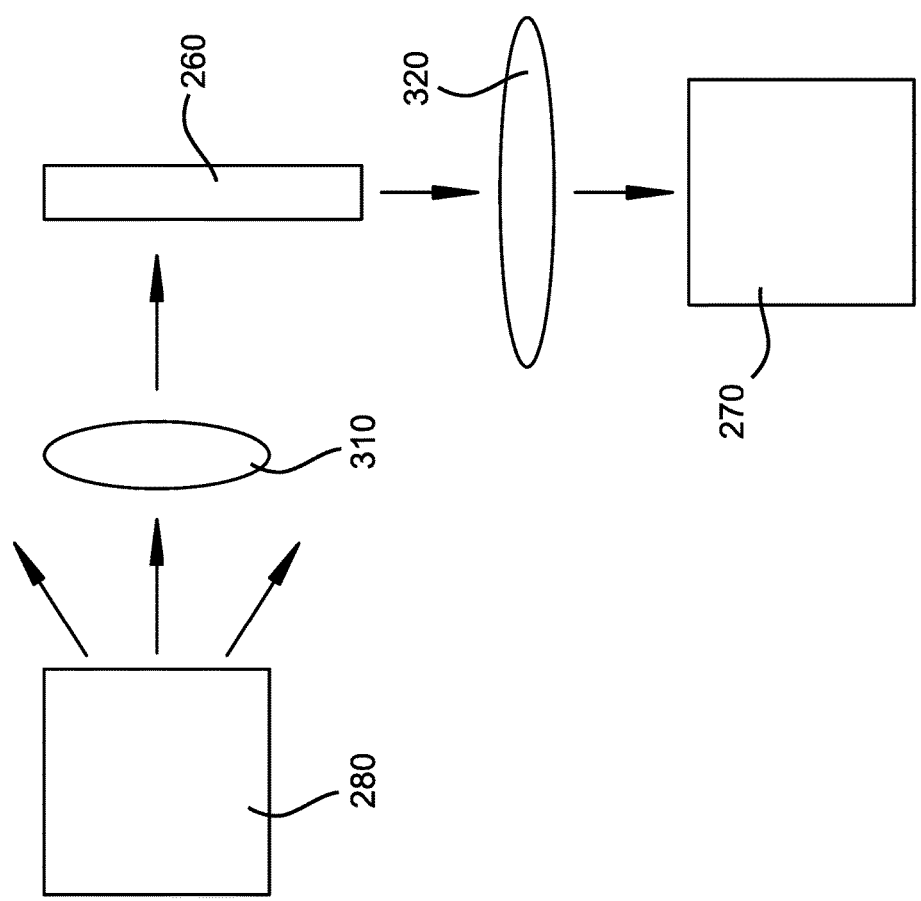
FIG. 3A is a schematic drawing of an embodiment of components of a fluorescence spectroscopy analysis system.

FIG. 3A illustrates an embodiment of a fluorescence spectrometer according to the disclosure in more detail. Fluorescence excitation light source 280 which emits light at multiple wavelengths which are directed toward a first filter 310. First filter 310 blocks out approximately all wavelengths of light except for those in a defined range or of a defined wavelength, the defined range or wavelength depending on the fluorescent marker to be measured. The filtered light then passes through fluorescence measurement cell 260, thereby exciting fluorescent markers in the urine that are excitable by light of the defined wavelengths. The fluorescent markers then emit fluorescent light of a certain wavelength(s). The emitted fluorescent light travels through second filter 320 which filters out approximately all wavelengths of light except for those to be measured. In this way, the wavelength of emitted fluorescent light that a marker associated with a particular drug may be measured by fluorescence spectral analyzer 270 without interference by signals from other markers.

Figure 3B:
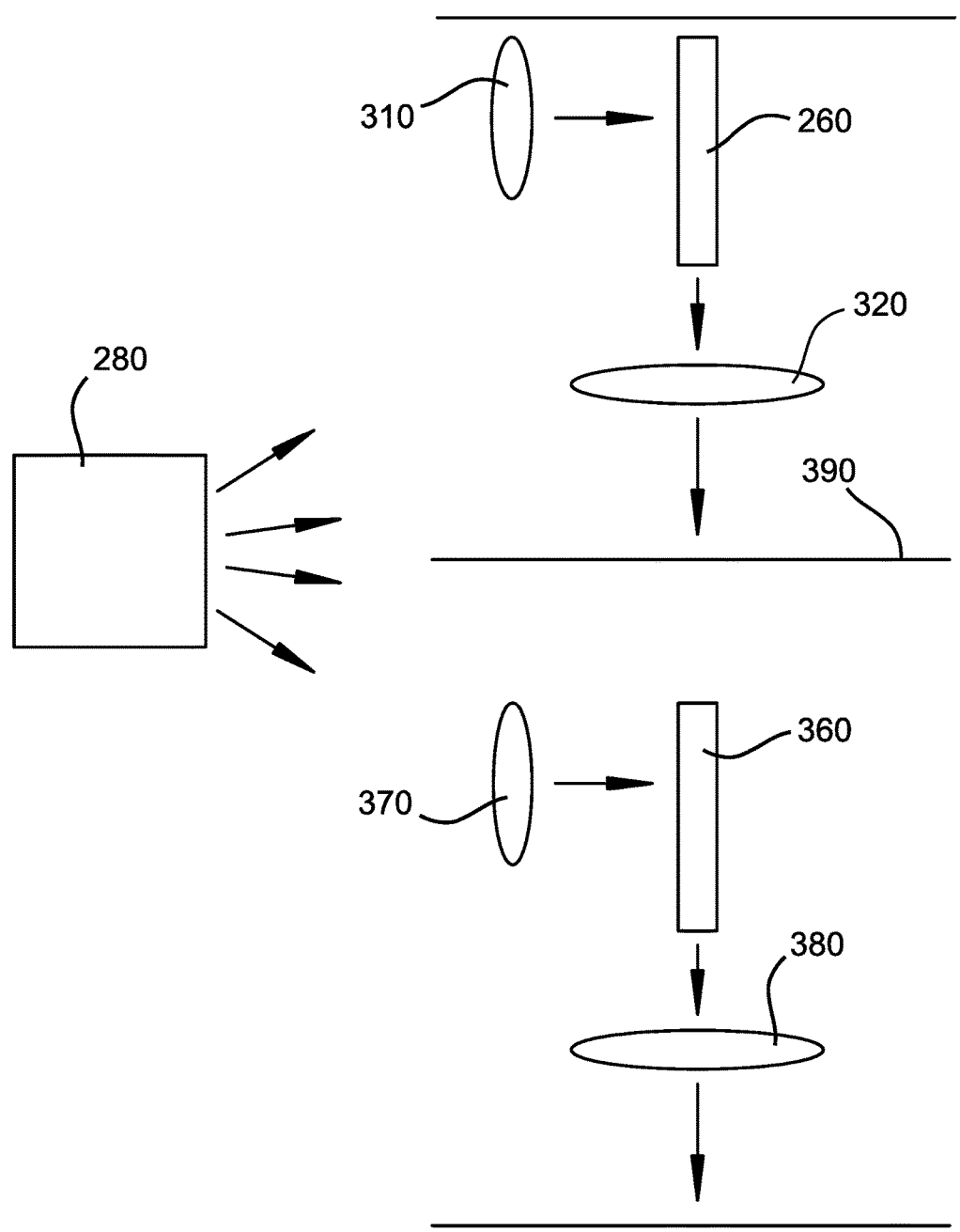
FIG. 3B is a schematic drawing of an embodiment of components of a fluorescence spectroscopy analysis system.

FIG. 3B illustrates a second embodiment of a fluorescence spectrometer according to the disclosure which includes the components of the fluorescence spectrometer shown in FIG. 3A. The embodiment of FIG. 3B further includes third filter 370 which functions analogous to first filter 310, a second fluorescence measurement cell 260. The embodiment of FIG. 3B further includes fourth filter 380 which functions analogous to second filter 320. Partition 390 divides the two sets of filters and the two fluorescence measurement cells so that stray light form one system is not detected by the other system. Emitted fluorescent light from each of fluorescence measurement cells 260 and 360 may be detected by a spectral analyzer (for clarity, not shown). The spectral analyzer may sequentially measure the emissions from fluorescence cells 260 and 360 or may be designed to simultaneously detect multiple fluorescence emissions with filters or partitions in place to prevent stray light crossing over from the two fluorescence measurement cells.

Figure 3C:
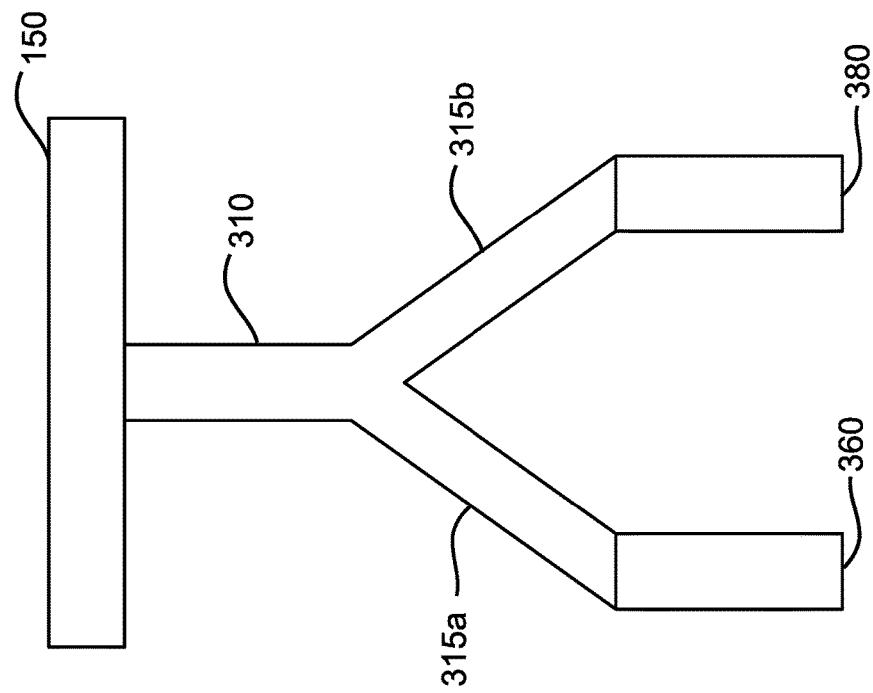
FIG. 3C is a schematic drawing of an embodiment of a urine sampling mechanism for loading urine into dual fluorescence measurement cells.

FIG. 3C illustrates an embodiment of a urine capture reservoir and a fluid handling system that diverts urine into two fluorescence measurement cells which may be the system illustrated in FIG. 3B. The embodiment of FIG. 3C includes orifice 150 through which urine travels into chamber 310. Chamber 310 then divides into two branches, branch 315a and 315b. Urine travels through branch 315a into fluorescence measurement cell 360 and urine travels through branch 315b into fluorescence measurement cell 380. Markers in the separated urine sample may be analyzed as described in the discussion of FIG. 3B or other embodiments thereof.

Figure 4A:
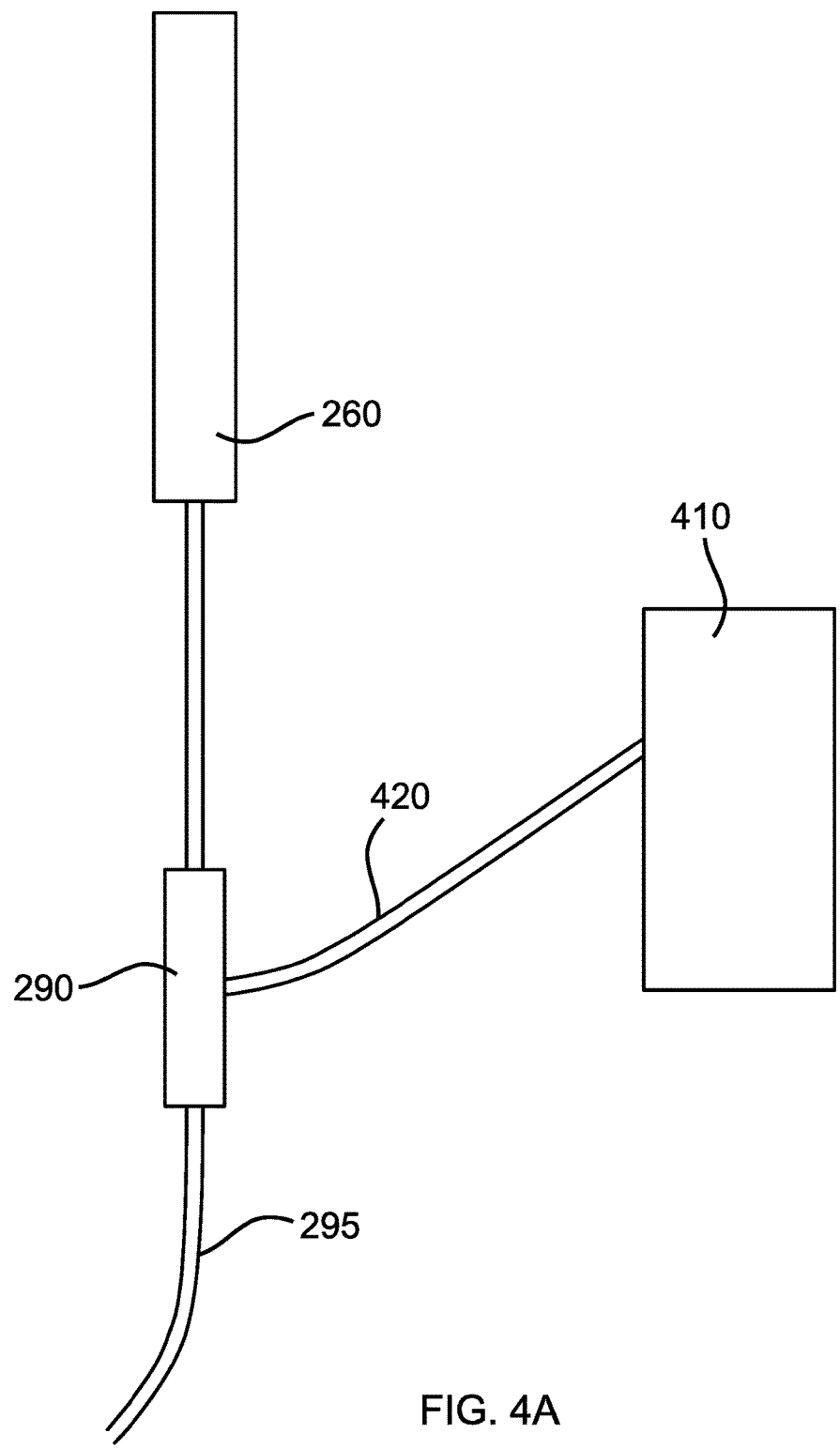
FIG. 4A is a schematic drawing of a rinsing device including a valve according to an embodiment of the invention.
Figure 4B:
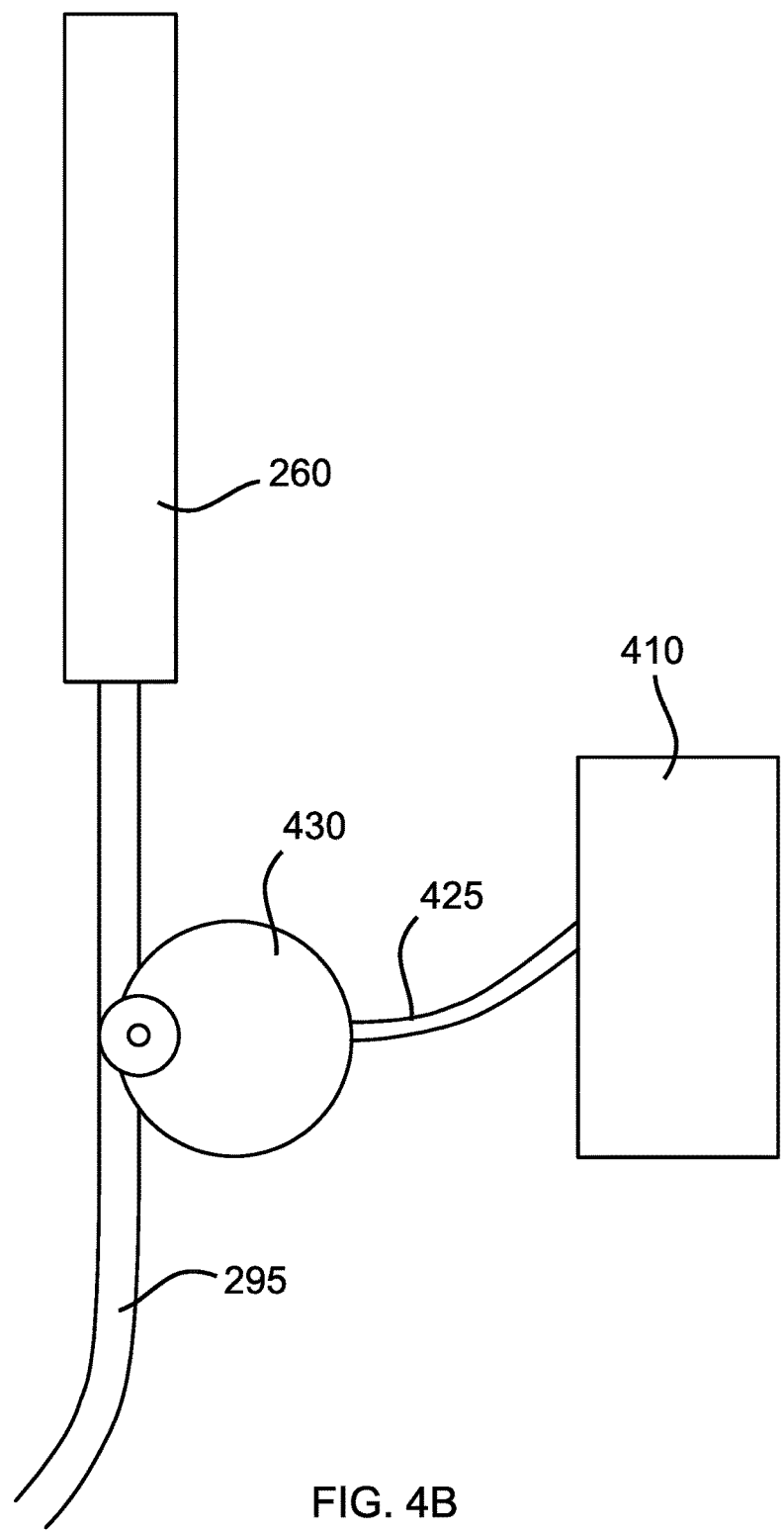
FIG. 4B is a schematic drawing of a rinsing device including a pump according to an embodiment of the invention.

FIGS. 4A and 4B illustrate two different embodiments of the rinsing device. FIG. 4A illustrates an embodiment of the rinsing device which includes valve 290. In this embodiment, valve 290 is positioned within the rinsing device between the water source and the fluorescence measurement cell 260. Valve 290 may open and close tubing 295 which is connected to the water source. In the embodiment shown in FIG. 4A, valve 290 is connected to controller 410 through connector 420. Controller 410 controls the opening and closing of valve 410 so that it is closed when the urine is being analyzed and opened after analysis is complete and it is time to flush out the system.

FIG. 4B illustrates another embodiment of the rinsing device which includes a pump 430. In this embodiment, pump 430 is a peristaltic pump which is connected to controller 410 by connector 425. Controller 410 actuates pump 430 to direct water from the water source through tubing 295 after an analysis of urine is complete to rinse out the system before the next user. Controller 410 stops pump 430 during analysis of urine. Some embodiments include both a pump and a valve in the rinsing device. Furthermore, some embodiments may include other types of pumps known in the art.

Figure 5:
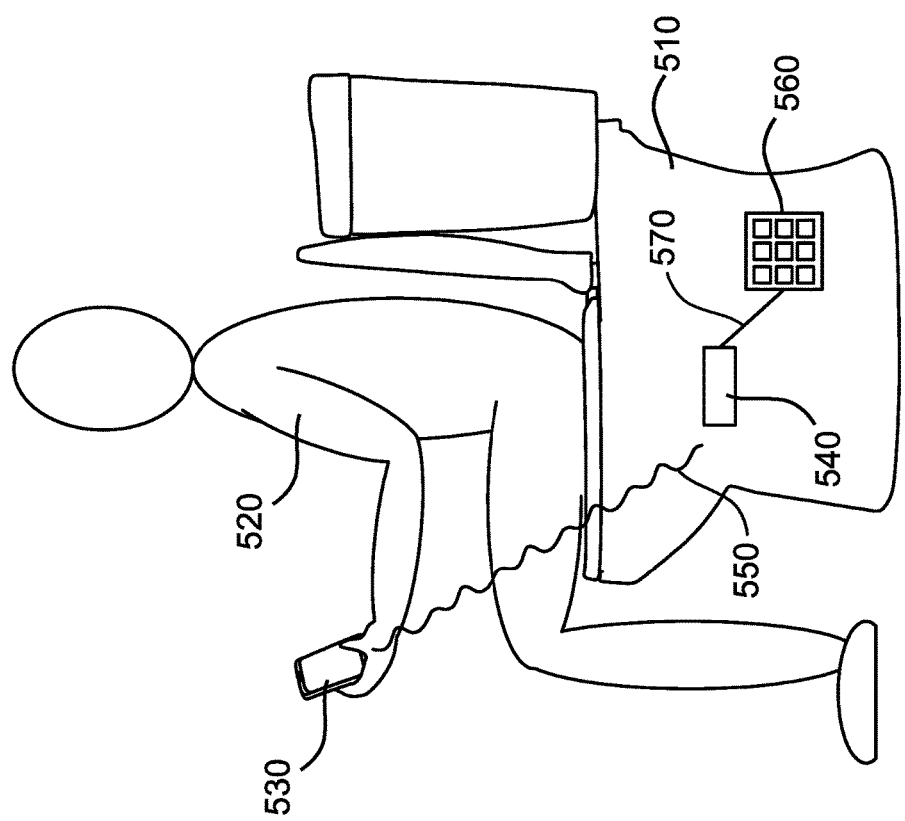
FIG. 5 is a schematic drawing of a user on a toilet according to an embodiment of the invention illustrating embodiments of user identification mechanisms.

FIG. 5 illustrates user 520 in the process of urinating in toilet 510 which is an embodiment of the disclosure. Toilet 510 includes multiple mechanisms for detecting a user's identity. User 520 is holding mobile device 530. Mobile device wirelessly communicates with controller 540 to provide the controller with the user's identity. The wavy line connecting mobile device 530 with controller 540 represents the wireless signal.

In addition, toilet 510 includes keypad 560 which is also connected to controller 540 through wiring 570. User 520 could enter a keycode into keypad 560 to provide identity information which is then transferred to controller 540. By providing user identity information, toilet 510 may collect multiple analyses and assign each to the user who provided the urine sample.

In addition to a user's mobile device or a keypad, other embodiments of the disclosed toilet may use other methods to identify a user. Some embodiments may use biometric verification methods, including fingerprint, iris, facial recognition, voice recognition, or electrocardiogram readings. Alternatively, the toilet may identify the user by unique user health signatures including measurement of body weight, bio-impedance, or urine flow rate.

In some embodiments, the controller is connected to a network database. Data collected by the toilet, along with associated user identity information, may be uploaded from the controller in the toilet to the network database. Uploading may be performed wirelessly, through an Ethernet, or other methods known in the art. The data may then be downloaded to a computer at a remote location for analysis. The analysis may be performed by a healthcare provider, law enforcement in the case of screening for illicit drugs, investigators conducting medical studies, or others who may have use for the data. In these embodiments, the controller within the toilet includes a data communication port.

Figure 6:
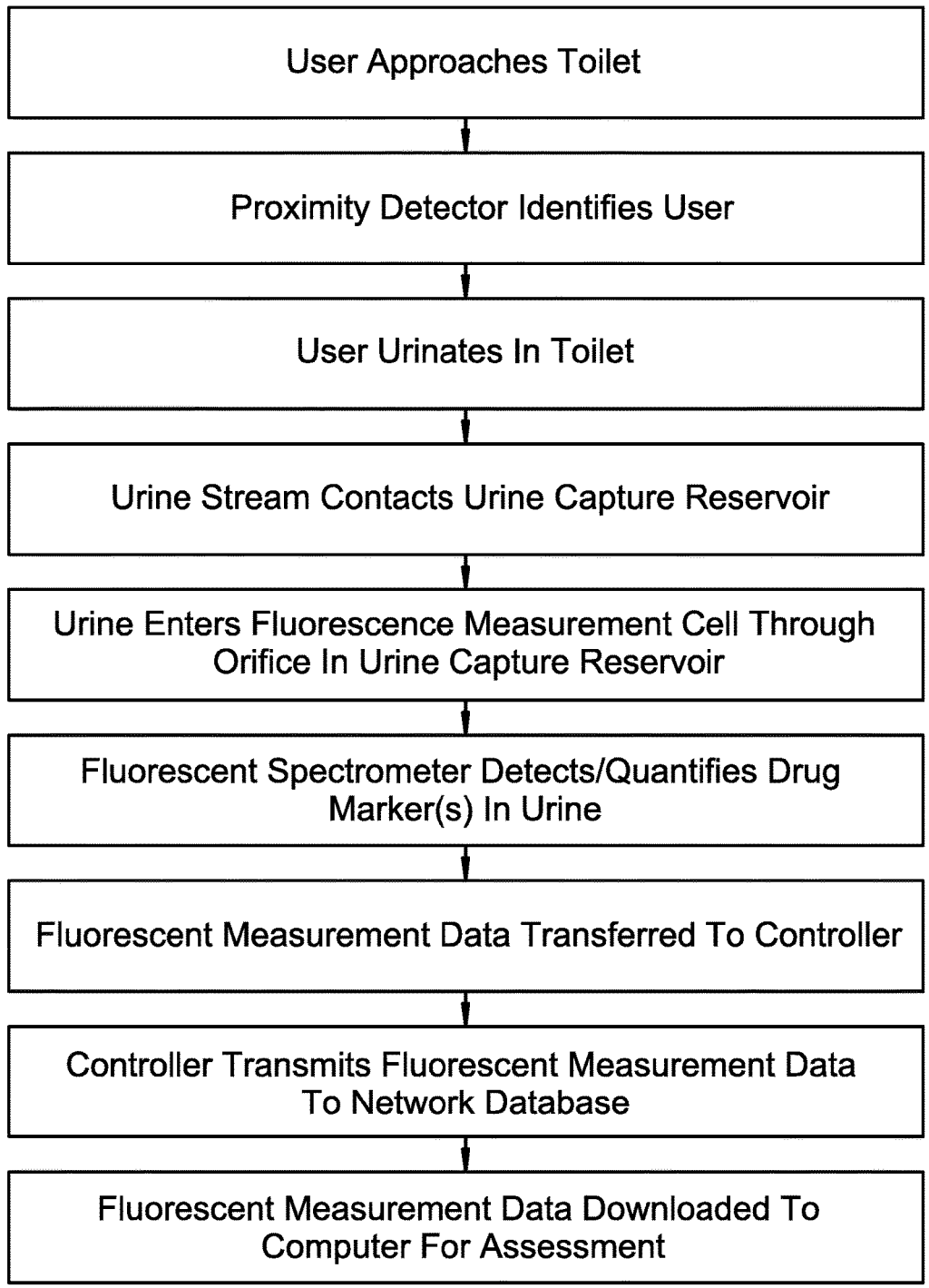
FIG. 6 is a flow chart illustrating an embodiment of a method of using the disclosed invention.

FIG. 6 is a flow chart illustrating one embodiment of a method of using the disclosed toilet. In this embodiment, the toilet is equipped with a proximity detector which, upon detecting the presence of a user, also provides user identity data. The proximity detector identifies the user as the user approaches the toilet. The user then urinates in the toilet and at least some of the urine is collected by the urine capture reservoir. Some of the urine enters the fluorescence measurement cell through the orifice in the urine capture reservoir. The fluorescence spectrometer measures the fluorescence emissions from drug markers in the user's urine. The data is transferred to the controller where it may be processed to identify and or quantify the drug marker and then to a network database. The fluorescence data is then downloaded to a remote computer for analysis to assess the user's drug consumption. The fluorescence emission spectrum reading may be associated with the unique fluorescence emission spectra of a known drug marker. Thus, the identity of the drug may be associated with the identity of the drug marker.

While specific embodiments have been described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method for detecting at least one drug marker in urine comprising the steps of:
    providing a toilet, the toilet comprising:
        a urine capture reservoir,
        a fluorescence spectrometer, the fluorescence spectrometer comprising:
            at least one fluorescence excitation light source,
            at least one fluorescence measurement cell, and
            a spectral analyzer;
        a channel, wherein the channel fluidly connects the urine capture reservoir to the at least one fluorescence measurement cell;
        a controller, the controller comprising a non-transitory computer readable medium and, wherein the controller is connected to the fluorescence spectrometer;
    depositing a urine sample produced by a user's body into the toilet,
        wherein at least a portion of the urine sample enters the urine capture reservoir, travels through the channel, and enters the at least one fluorescence measurement cell,
        wherein the user has consumed a composition,
        wherein the composition comprises at least one drug, at least one fluorescent drug marker, and a liposome carrier,
        wherein the at least one drug is encapsulated within the liposome carrier,
        wherein the at least one fluorescent drug markers emits a unique fluorescence emission spectra relative to other fluorescent drug markers when exposed to light of a defined wavelength.

2. The method of claim 1, wherein the fluorescent drug marker is encapsulated in the liposome carrier.

3. The method of claim 2, wherein the liposome comprises a ligand, and wherein the ligand targets a tissue in which is a target of the drug.

4. The method of claim 1, wherein the composition comprises a plurality of drugs.

5. The method of claim 1, wherein the toilet consists of a device for a deposition of human or animal waste.

6. A method for detecting at least one drug marker in urine comprising the steps of:
    providing a toilet, the toilet comprising:
        a urine capture reservoir,
        a fluorescence spectrometer, the fluorescence spectrometer comprising:
            at least one fluorescence excitation light source, at least one fluorescence measurement cell, and
a spectral analyzer;
a channel, wherein the channel fluidly connects the urine capture reservoir to the at least one fluorescence measurement cell;

depositing a urine sample produced by a user's body into the toilet,
wherein at least a portion of the urine sample enters the urine capture reservoir, travels through the channel, and enters the at least one fluorescence measurement cell,
wherein the user has consumed a composition,
wherein the composition comprises at least one drug, and at least one quantum dot,
wherein the at least one quantum dot is functionalized by coating or connecting the at least one quantum dot to a biomolecule, wherein the biomolecule is cleavable by a peptidase, a protease, or a nuclease,
wherein the at least one quantum dot emits a unique fluorescence emission spectra relative to other fluorescent drug markers when exposed to light of a defined wavelength.

7. The method of claim 6, wherein the biomolecule is cleavable by a eukaryotic single strand DNA nuclease.

8. The method of claim 7, wherein the eukaryotic single strand nuclease is selected from the group consisting of a zinc finger nuclease, RNAse H2, pancreatic nuclease, and p53.

9. The method of claim 6, wherein the biomolecule is cleavable by DNAse I.

10. The method of claim 6, wherein the biomolecule is cleavable by a eukaryotic protease.

11. The method of claim 9, wherein the eukaryotic protease is selected from the group consisting of a metalloprotease, a serine protease, a digestive protease.

12. The method of claim 11, wherein the digestive protease is selected from the group consisting of gastrin, pepsin, trypsin, and chymotrypsin.

13. The method of claim 11, wherein the serine protease is selected from the group consisting of thrombin, plasmin, and urokinase.

14. The method of claim 6, wherein the biomolecule is cleavable by a glycoside hydrolase.

15. The method of claim 14, wherein the glycoside hydrolase consists of lysozyme.

16. The method of claim 6, wherein the biomolecule is cleavable by an enzyme derived from *Escherichia coli*.

17. The method of claim 16, wherein the enzyme derived from *Escherichia coli* is selected from the group that consists of exonuclease I, exonuclease IV, RNAse A, and RNAse I.

18. The method of claim 6, wherein the biomolecule comprises a hydrogel.

19. The method of claim 18, wherein the hydrogel is cleaved by a solution comprising a pH of between about 1.0 and about 3.0.

20. The method of claim 6, wherein the composition comprises a plurality of drugs.

* * * * *